(12) United States Patent
Diamond et al.

(10) Patent No.: US 8,591,722 B2
(45) Date of Patent: Nov. 26, 2013

(54) METHOD FOR DETERMINATION OF ANALYTE CONCENTRATIONS AND RELATED APPARATUS

(75) Inventors: Steven Diamond, San Francisco, CA (US); Ian Harding, Wells (GB); Sridhar G. Iyengar, Salem, NH (US); Baoguo Wei, Salem, NH (US)

(73) Assignee: AgaMatrix, Inc., Salem, NH (US)

( * ) Notice: Subject to any disclaimer, the term of this patent is extended or adjusted under 35 U.S.C. 154(b) by 0 days.

(21) Appl. No.: 13/206,010

(22) Filed: Aug. 9, 2011

(65) Prior Publication Data

US 2011/0290673 A1 Dec. 1, 2011

Related U.S. Application Data

(62) Division of application No. 12/685,788, filed on Jan. 12, 2010, now Pat. No. 8,016,997, which is a division of application No. 10/907,815, filed on Apr. 15, 2005, now Pat. No. 7,645,374.

(51) Int. Cl.
*G01N 27/327* (2006.01)
*G01R 23/02* (2006.01)

(52) U.S. Cl.
USPC ...... 205/775; 702/23; 324/76.39; 204/403.01

(58) Field of Classification Search
USPC ............... 204/400, 403.01–403.07, 204/403.1–403.15; 205/775, 777.5, 792; 600/345–347, 365; 702/22, 23, 30, 702/108, 116; 73/61.41; 324/713, 76.39
See application file for complete search history.

(56) References Cited

U.S. PATENT DOCUMENTS

| | | |
|---|---|---|
| 5,243,516 A | 9/1993 | White |
| 5,266,179 A | 11/1993 | Nankai et al. |
| 5,320,732 A | 6/1994 | Nankai et al. |
| 5,352,351 A | 10/1994 | White et al. |
| 5,438,271 A | 8/1995 | White et al. |
| 5,582,697 A | 12/1996 | Ikeda et al. |
| 5,942,102 A | 8/1999 | Hodges et al. |
| 6,284,125 B1 | 9/2001 | Hodges et al. |
| 6,413,411 B1 | 7/2002 | Pottgen et al. |
| 6,428,684 B1 | 8/2002 | Warburton |

(Continued)

FOREIGN PATENT DOCUMENTS

| | | |
|---|---|---|
| EP | 1236995 A | 9/2002 |
| EP | 1318399 A | 6/2003 |

(Continued)

OTHER PUBLICATIONS

Malmstadt, H. V., et al, "Microcomputer and Electronic Instrumentation: Making the Right Connection.", American Chemical Society, 1994, pp. 219-221.

*Primary Examiner* — J. Christopher Ball
(74) *Attorney, Agent, or Firm* — Larson & Anderson, LLC

(57) ABSTRACT

A method is provided for determining analyte concentrations, for example glucose concentrations, that utilizes a dynamic determination of the appropriate time for making a glucose measurement, for example when a current versus time curve substantially conforms to a Cottrell decay, or when the current is established in a plateau region. Dynamic determination of the time to take the measurement allows each strip to operate in the shortest appropriate time frame, thereby avoiding using an average measurement time that may be longer than necessary for some strips and too short for others.

5 Claims, 7 Drawing Sheets

(56) References Cited

U.S. PATENT DOCUMENTS

| | | |
|---|---|---|
| 6,616,819 B1 | 9/2003 | Llamos et al. |
| 2002/0053523 A1 | 5/2002 | Llamos et al. |
| 2003/0106809 A1 | 6/2003 | Kermani et al. |
| 2003/0145644 A1 | 8/2003 | Rabbett et al. |
| 2003/0178322 A1 | 9/2003 | Iyengar et al. |
| 2004/0259180 A1 | 12/2004 | Burke et al. |
| 2005/0067301 A1 | 3/2005 | Morita et al. |
| 2005/0069892 A1 | 3/2005 | Iyengar et al. |
| 2005/0109637 A1 | 5/2005 | Iyengar et al. |
| 2005/0258034 A1 | 11/2005 | Iketaki et al. |
| 2006/0182658 A1* | 8/2006 | Wu et al. .................. 422/68.1 |

FOREIGN PATENT DOCUMENTS

| | | |
|---|---|---|
| WO | 03060154 A2 | 7/2003 |
| WO | 03069304 A2 | 8/2003 |
| WO | 2005022143 | 8/2004 |

* cited by examiner

METHOD FOR DETERMINATION OF ANALYTE CONCENTRATIONS AND RELATED APPARATUS

BACKGROUND

This application relates to a method for detection of analyte concentration using an electrochemical test strip, and to a meter and meter test strip combination for use in such a method.

Small disposable electrochemical test strips are frequently used in the monitoring of blood glucose by diabetics. Such test strips can also be employed in the detection of other physiological chemicals of interest and substances of abuse. In general, the test strip comprises at least two electrodes and appropriate reagents for the test to be performed, and is manufactured as a single use, disposable element. The test strip is combined with a sample such as blood, saliva or urine before or after insertion in a reusable meter, which contains the mechanisms for detecting and processing an electrochemical signal from the test strip into an indication of the presence/absence or quantity of the analyte determined by the test strip.

Electrochemical detection of glucose is conventionally achieved by applying a potential to an electrochemical cell containing a sample to be evaluated for the presence/amount of glucose, an enzyme that oxidizes glucose, such as glucose oxidase, and a redox mediator. As shown in FIG. 1, the enzyme oxidizes glucose to form gluconolactone and a reduced form of the enzyme. Oxidized mediator reacts with the reduced enzyme to regenerate the active oxidase and produce a reduced mediator. Reduced mediator is oxidized at one of the electrodes, and then diffuses back to either be reduced at the other electrode or by the reduced enzyme to complete the cycle, and to result in a measurable current. The measured current is related to the amount of glucose in the sample, and various techniques are known for determining glucose concentrations in such a system. (See, U.S. Pat. Nos. 6,284,125; 5,942,102; 5,352,2,351; and 5,243,516, which are incorporated herein by reference.)

Improvements in test strip design are driven by several considerations, including the need for accuracy and a desire for production of rapid results. The time required for correct measurement to occur, however, can be variable as a result of sample characteristics and variabilty of the test device. Thus, devices which perform a measurement at a fixed time after sample insertion have to make compromises in order to maximize the likelihood of sufficient time having passed. This compromise lengthens the time required to do a measurement, and may still fail to deal with samples and test devices that fail to conform to anticipated averages. Since performance of duplicate tests requires a level of user participation that may not be obtained, it would be desirable to have a glucose test system that did not make these compromises.

SUMMARY OF THE INVENTION

The present application provides a method for determining analyte concentrations, for example glucose concentrations, that utilizes a dynamic determination of the appropriate time for making a glucose measurement, for example when a current versus time curve substantially conforms to a Cottrell decay, or when the current is established in a plateau region.

When determining analyte from a measurement of Cottrell current, the starting time, $t_{meas}$ for the measurement is established dynamically at a time after $t_{peak}$ when the observed current profile substantially conforms to Cottrell decay. In specific embodiments, this time set is a multiple of the time of maximum observed current, $t_{peak}$, where the multiple is determined for a given test strip configuration. In other embodiments, the $t_{meas}$ is $t_{peak}$+a constant, for example plus 1.5 to 2.5 seconds. In the general case, $t_{meas}=a_1 \times t_{peak}+a_2$ with either or both of empirically determined constants being utilized. Making glucose determinations based on the observed currents at these times results in determinations with improved reliability, and also minimizes the time required for sample evaluation for any given sample. Thus, the method of the invention provides superior performance and more robust results.

When making measurements in the plateau region, the starting time $t_{meas}$ is determined once the change in current with time has passed below a predetermined threshold value, or may be determined as either $t_{peak}$ plus a constant or $t_{peak}$ times a constant. The numerical values of these constants in each case are determined empirically for a given test strip and meter, since the optimum time will depend on factors such as electrode spacing and chemistry, and the applied voltage.

The present invention also provides an apparatus with appropriate electronic components for dynamic determination of the location of $t_{peak}$, and for collection of current data at the desired time thereafter. The apparatus has a housing with a slot for introduction of an electrochemical test strip, means for communicating/displaying a determined analyte level to a user, and the necessary electronics to process the sample and convert measured values into a communicated/displayed analyte level. The invention further provides a combination of such a meter with an electrochemical test strip.

The value of $t_{peak}$ can also be used to check for errors in the measurement which leads to an error indication from the meter. For example, if $t_{peak}$ is outside of an empirically determined range, then an error state should be established by the meter.

DETAILED DESCRIPTION OF THE INVENTION

I. Definitions

Figure 1:
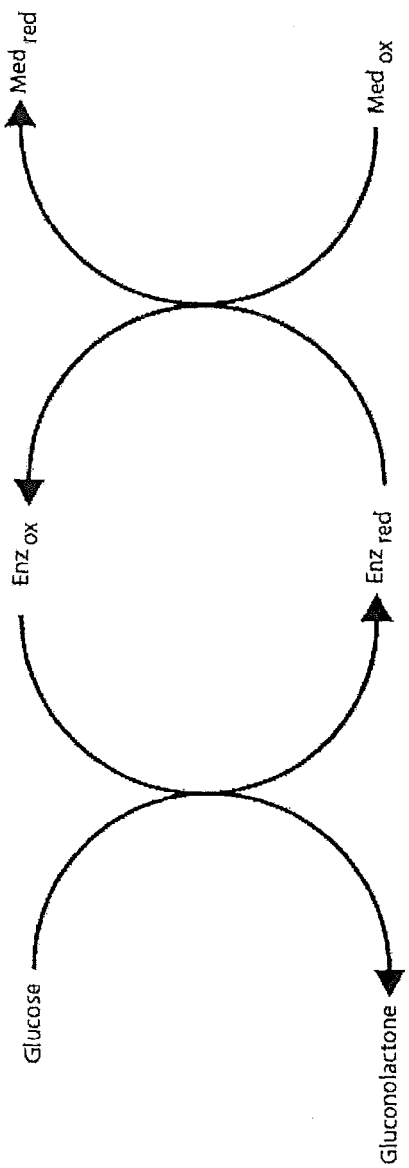
FIG. 1 shows the electron transfer reactions that occur in a conventional amperometric glucose detector.

As used in the specification and claims of this application, the following definitions should be applied:

(a) "analyte" refers to a material of interest that may be present in a sample. In the present application, the examples use glucose as an analyte, but the present invention is independent of both the type and amount of analyte. Accordingly, application to glucose detection systems should be viewed as merely a specific and non-limiting embodiment. In some cases, there may be one or more intermediate species between the actual analyte and the mediator. Any such intermediate species are also referred to herein as an analyte.

(b) "Cottrell decay" or "Cottrell current" is current that can be modeled by the Cottrell equation, i.e., $$1/I^2 \propto t$$

where I is the current and t is time. The square root of the slope of $1/I^2$ versus t is a parameter called the "Cottrell slope."

(c) "determination of an analyte" refers to qualitative, semi-quantitative and quantitative processes for evaluating a sample. In a qualitative evaluation, a result indicates whether or not analyte was detected in the sample. In a semi-quantitative evaluation, the result indicates whether or not analyte is present above some pre-defined threshold. In a quantitative evaluation, the result is a numerical indication of the amount of analyte present.

(d) "electrochemical test strip" refers to a strip having at least two electrodes, and any necessary reagents for determination of an analyte in a sample placed between the electrodes. In preferred embodiments, the electrochemical test strip is disposable after a single use, and has connectors for attachment to a separate and reusable meter that contains the electronics for applying potential, analyzing signals and displaying a result.

(e) "facing electrodes" are a pair of electrodes disposed parallel to but in a separate plane from each other. Some or all of the opposed surfaces of a pair of facing electrodes overlap, such that potential gradients and current flows between the electrodes are in a direction substantially perpendicular to the opposed surfaces. Facing electrodes are distinguished from side-by-side electrodes in which the two electrode surfaces lie in the same plane, and in which potential gradients and current flow is substantially parallel to the surface of the electrodes. The present invention can be used with either facing or side-by-side electrodes.

(f) "dynamic determination" refers to the determination of a value during the course of the measurement cycle for a particular sample. For example, dynamic determination of the time $t_{peak}$ determines that time at which maximum current occurs during the course of the measurement cycle of the sample being processed in the individual test strip, exclusive of any initial current spike associated with double-layer charging.

(g) "mediator" refers to a chemical species that is electrochemically detected. Numerous electron transfer mediators suitable for detection of analytes such as glucose are known, and include without limitation iron, ruthenium, and osmium compounds. In some embodiments of the invention, the mediator is produced through one or more reaction steps and is related to the concentration of the actual analyte, such as glucose. The present invention is also applicable, however, to circumstances in which the detected chemical species is the reduced form of the analyte to be detected, and this is also an embodiment of the invention.

(h) "$t_{meas}$" refers to the time at which a measurement of current is made for purposes of obtaining data for determination of an analyte. In a Cottrell measurement where the Cottrell slope is to be determined, at least two data points at different times are required. In this case, $t_{meas}$ refers to the start or center of the measurement window, whichever conditions are used in determining the empirical constants. Where a single data point is sufficient, for example when a plateau current is measured, $t_{meas}$ refers to the time at which this data point is taken.

(i) "$t_{peak}$" is the time at which maximum current occurs during the course of the measurement cycle of the sample being processed in the individual test strip, exclusive of any initial current spike associated with double-layer charging. This peak current occurs at the point of changeover when sufficient material is available at the counter electrode to balance the consumption of analyte or mediator at the working electrode. At this point, the consumption of analyte or mediator at the working electrode becomes limiting. This rapid fall in current that results from the diffusion-limited consumption of analyte is what gives rise to the characteristic Cottrell decay.

II. Detection of Analyte, for Example Glucose

Figure 2:
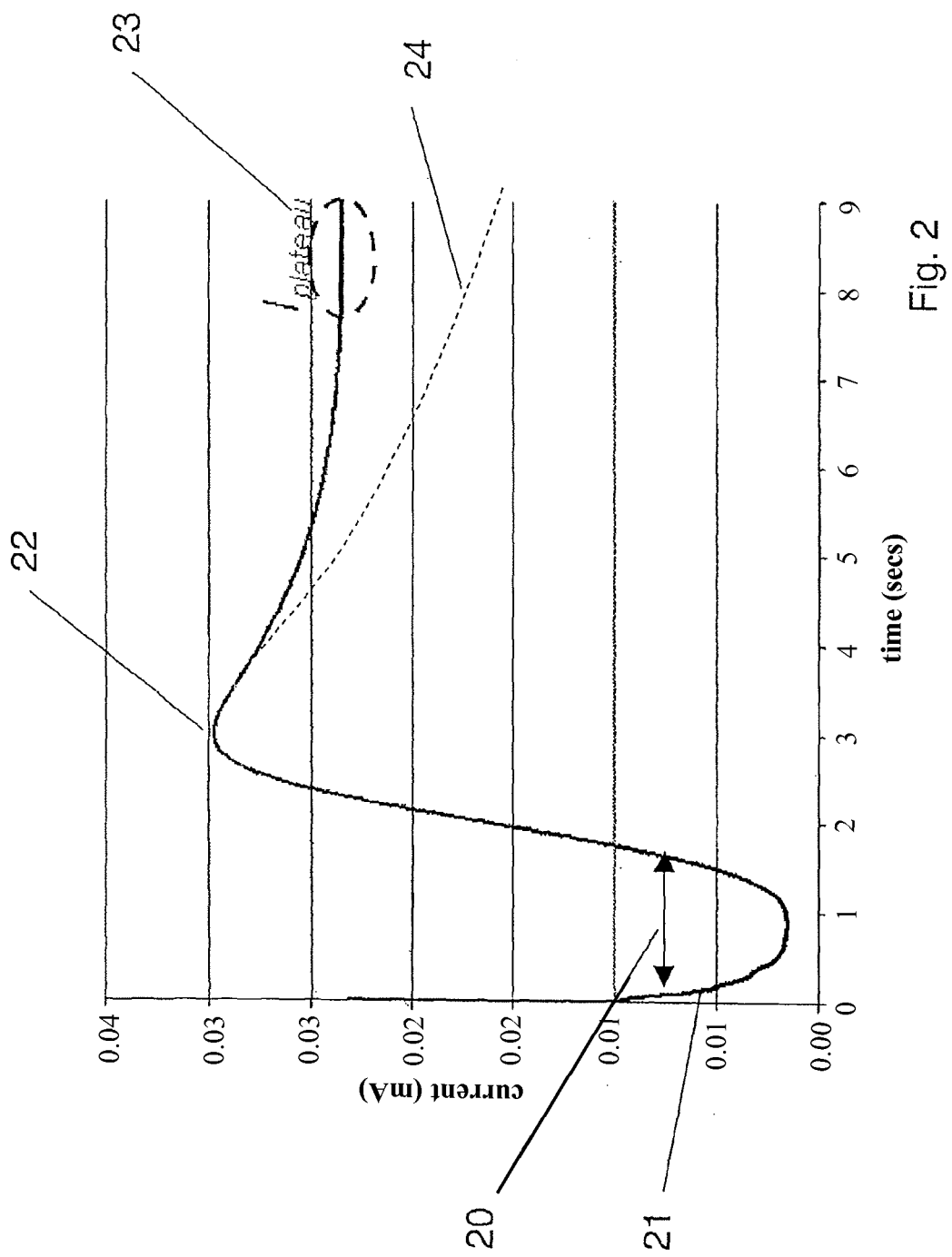
FIG. 2 show the type of current versus time profiles observed in two different electrochemical test strip configurations.

FIG. 2 shows current versus time profiles observed in two different electrochemical test strip configurations, one with facing electrodes and one with side-by-side electrodes, where the electrochemical reagents are initially disposed only on the working electrode, and not on the counter electrode. In both cases, the current trace shows an immediate initial current 21 on the time scale shown following application of the potential. This current is associated with the initial charging of the double layer at the surface of the electrodes. Thereafter, the current decreases, because current is dependent on the mediator diffusing from the working electrode (where the reagent comprising the mediator was deposited during manufacture) to the counter electrode. The duration of this reduced current (indicated by arrow 20) is dependent on the distance between the electrodes, and on the mobility of the mediator. Mediator mobility is a property of the mediator itself, i.e., the diffusion coefficient, but is also dependent on other sample properties such as hematocrit and viscosity. After the period of reduced current 20, the current rapidly rises to a peak current 22. In the case of facing electrodes, the current declines to a plateau current 23 which reflects the recycling or shuttling of mediator between the electrodes. In the case of side-by-side electrodes, the current continues to decay in the time scale indicated, as indicated by dashed line 24. At longer times, this curve 24 may also shows effects of recycling/shuttling of mediator if the electrodes are placed close enough together.

In the region of the decay following the peak, before recycling becomes dominant, the current decay can be modeled by the Cottrell equation, i.e., $$1/I_2 \propto t$$

where I is the current and t is time. Cottrell analysis can be utilized to determine glucose concentration as described in U.S. Pat. Nos. 5,243,516; 5,352,351 and 6,284,125. Commonly assigned U.S. patent application Ser. No. 10/907,803, which is incorporated herein by reference, discloses a Cottrell analysis of analyte concentration that includes a mobility correction obtained when the applied potential is switched off after monitoring the current to obtain data for determination of analyte.

As an alternative to Cottrell analysis, current in the plateau region 23 of FIG. 2 can be used to determine analyte concentration. This type of measurement is particularly applicable when using conduction cell test strips, as described in commonly assigned U.S. patent application Ser. No. 10/924,510, which is incorporated herein by reference.

In determining the numerical value of analyte concentration which is communicated/displayed to a user, one or more correction factors based on calibration values for a lot of strips, or measurements made during the analysis may be applied. Further, it will be understood that a look up table or other conversion system may be used to convert a raw value into a meaningful value for communication/display to the user.

III. Determination of $t_{peak}$

The present invention uses a determination of $t_{peak}$ as a basis for a dynamic determination of the time, $t_{meas}$, at which measurement will be made or commenced.

In accordance with the invention, a sample in a electrochemical test strip is processed to generate a current profile as shown in either line in FIG. 2. Thus, in a first step, a diffusion-limiting voltage is applied to a test strip rapidly after a sample is introduced to the chamber. The polarity of the electrodes is such that a first electrochemically detectable species whose concentration depends on the analyte will be consumed at the electrode the reagent is deposited on one electrode (the 'working electrode', and balanced by a counter reaction of a second species in excess in the reagent at the opposite electrode (the 'counter electrode'). In this way, a signal limited by consumption of the first species will not occur until there is excess of the second species at the opposite electrode, a condition that is limited by mobility. The voltage applied to the test strip to stimulate a current through the sample should be sufficiently high to ensure the current reaches a limit set by the mobility of species, the so-called "diffusion limited current." Further, this voltage needs to have been applied sufficiently early that the change from current limited by arrival of species at the counter electrode to current limited by arrival of analyte-dependant species (analyte or mediator) at the working electrode can be observed under diffusion-limited conditions.

The initial current surge associated with application of the potential (due to establishing electrode double layers and consuming surface impurities) must have had sufficient time to die away to leave a baseline current that represents arrival of species at the counter electrode. This baseline is monitored and will start to increase rapidly when significant amounts of species become available to support reaction at the counter electrode. The rapid increase is monitored and a point of changeover noted. This changeover occurs when sufficient species are available to support reaction at the counter electrode to balance consumption of analyte-dependent species at the working electrode, which then becomes limiting. The time to this changeover is thus an indicator of mobility, and is designated in this application as $t_{peak}$. The change in limiting species results in the rapid consumption of analyte-dependent species near the working electrode and a rapid fall in the current as a result.

Identification of the peak is done by inspecting amperometric data as it is produced for a local maximum. Such inspection is best not started too early since filling, patient contact with the sample and initial current surges should be ignored: starting inspection from a time point of 1 to 2 seconds, for example 1.5 seconds after sample detection is adequate for most sub microliter electrochemical test strips. In one embodiment for the invention, the local maximum is the highest current in a time window from the present stretching back a set period: two seconds is good because it fits well with the time that must elapse for establishing a stable diffusion profile. When the local maximum is at the earliest point of the time window and has not been replaced by a higher maximum in later data, the peak can be assumed to have been identified as this local maximum. Identification can be improved further by applying digital or analogue filters to remove the effects of sharp spikes in the data that are not representative of diffusional processes. Other techniques, such as curve fitting to identify peaks of a particular expected form may also be used, or the amperometric signal can be evaluated to determine the time when the first derivative is zero.

In order to obtain a value for $t_{peak}$ which is an accurate measure of the time from the introduction of the sample, a mechanism for defining the start of the measurement cycle is required. As is apparent from looking at FIG. 2, the numerical value of $t_{peak}$ is dependent on the point in time which is assigned a zero value. If blood is applied to a test strip and a period of time is allowed to pass prior to starting the test cycle, enzyme and mediator will dissolve and tend to diffuse across evenly in the space between the electrodes. This will result in the shortening, if not the elimination of the interval 20. Thus, in practicing the method of the invention, it is important to have a consistent start time relative to sample application that is before diffusion to eliminate interval 20 can occur. In practice, this result can be obtained by automatically starting the cycle upon, or within a fixed period of time after the addition of sample to an electrochemical test strip that is already disposed in the meter.

Mechanisms for automatically starting the measurement cycle include, without limitation, (1) measuring a current or a resistance between the working and counter electrodes in the electrochemical test strip; and (2) measuring a current or a resistance between two electrodes wherein at least one of the two electrodes is not the working electrode or the counter electrode. Thus, the current or resistance could be measured between a combination of a third electrode and either the working or counter electrode, or between a third and fourth electrode. It will be appreciated that the current measured in this case can be a current in response to a low voltage, insufficient to produce redox chemistry indicative of analyte, although this requires a sample that has ionic charge carriers such as Na+ and Cl− either inherently present or added.

Sample detection to initiate timing of an assay may also be done passively as described in US Patent Publication US2003/0106809, which is incorporated herein by reference.

In one embodiment of the invention, while the meter is waiting for sample to be introduced after having been turned on by the user or by detection of a sample strip, it is pulsing the voltage, Vw, of the working electrode while holding the voltage, Vc, of the counter electrode constant. This pulsed voltage can conveniently be shaped almost as a sine wave using a low pass filter on Vw. The frequency of pulsing is dependent on the hardware chosen, and is suitably in the range of 20 to 50 Hz, for example 33 or 40 Hz.

When sample is introduced, the current traveling through the electrodes should spike with each pulse. To make a more reliable determination that sample has been introduced, however, in one embodiment of the invention, a plurality of consecutive spikes are required to count as an indication of sample application. For example, a positive indication of sample application may require a current spike in response to 3 of 4, 4 of 5, 4 of 6, or 6 of 8 consecutive voltage pulses.

Calculation of the starting time is based on an assumed sample application time prior to the triggering time. For example, in the case that 3 of 4 current spikes are required, it is assumed that sample was introduced 3 voltage pulses before the trigger. Therefore, the trigger happens at: t=(3/pulse frequency). In the case that 6 of 8 current spikes are required, it is assumed that sample was introduced 6 voltage pulses before the trigger. Therefore, the trigger happens at: t=(6/pulse frequency). The times $t_{peak}$ and $t_{meas}$ are determined with reference to this zero time.

Figure 4:
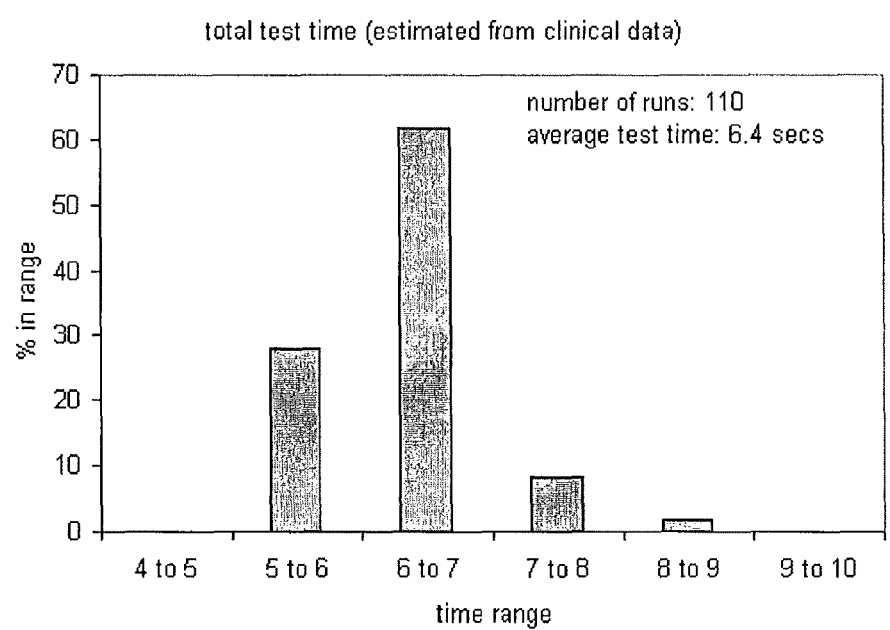
FIG. 4 shows projected run time in test strips which were intended for use with a Cottrell current measurement occurring at 8 sec.

While the Cottrell equation effectively models the decay of the current for a portion of the decay time following the peak current, the location of the peak is both sample and test strip dependent, and because the total duration of decay is short, it is difficult to statically determine a time that ensures measurements in this time zone in a practical working device. The same is true of plateau currents. The present application provides an improved method for determining when to perform the Cottrell or plateau analysis using a dynamic determination of $t_{peak}$. Accordingly, the present method allows each strip to operate in the shortest appropriate time frame, thereby avoiding using an average measurement time that may be longer than necessary for some strips and too short for others. (See FIG. 4 and Example 1 below).

IV. Determination of $t_{meas}$ for a Cottrell Analysis

Once $t_{peak}$ t is determined, this value may used to dynamically determine the time $t_{meas}$ at which the Cottrell decay should be sampled to assess glucose concentration. In a general sense, it is desirable to make the measurement at a time after $t_{peak}$ when the change in current over time most closely conforms to an ideal Cottrell decay. This can be accomplished in several ways, using either an analysis of collected current data in the time period following $t_{peak}$ or by setting $t_{meas}$ to be equal to $t_{peak}$ plus a predetermined number of seconds or times a predetermined factor, or a combination of both.

Figure 3A:
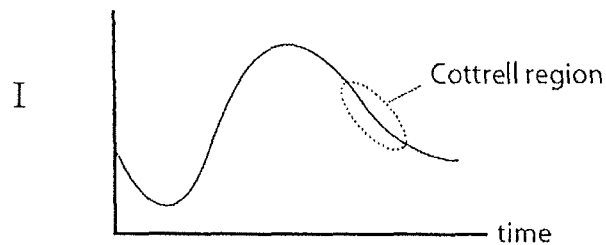
FIGS. 3A-D show signal processing options for locating a preferred $t_{meas}$ in a Cottrell analysis.
Figure 3B:
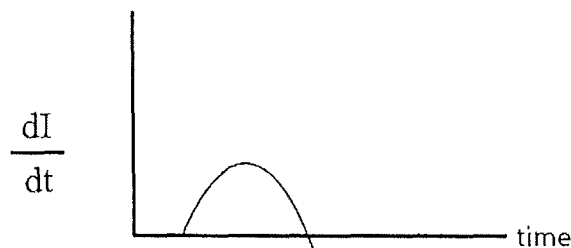
Figure 3C:
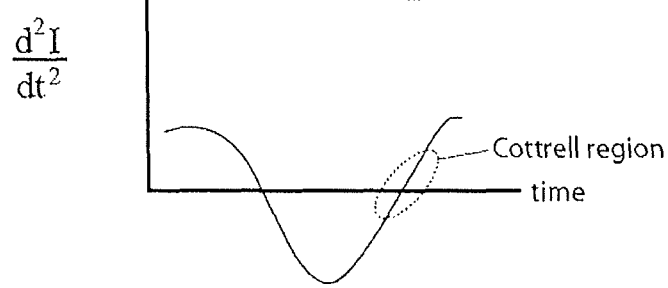
Figure 3D:
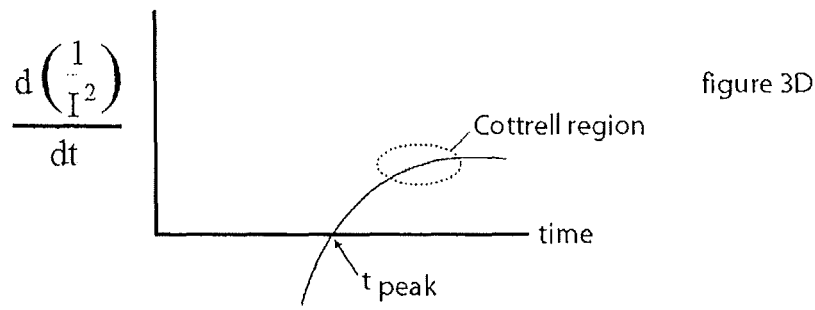

$t_{meas}$ can be established by analysis of collected data points in the time period following $t_{peak}$ t to determine a time when the signal conforms to Cottrell decay. FIGS. 3A-D outlines various signal processing options for accomplishing this result. FIG. 3A shows the unprocessed current as a function of time with the Cottrell region indicated. In one embodiment, the method involves processing the signal and identifying a local minimum in the first derivative. (FIG. 3B). In another embodiment, the second derivative of the current as a function of time (FIG. 3C) is evaluated and $t_{meas}$ is selected as the time at which the signal is substantially zero, for example −0.1 to 0.1. In yet another embodiment, the signal is processed to identify a maximum in $d(1/I^2)/dt$ (FIG. 3D).

As a practical alternative to processing the signal in this manner, it has been found that for a given specific electrochemical test strip, $t_{meas}$ can be defined as a simple multiple of $t_{peak}$ for example a multiple in the range of 1.2 to 1.4, for example between 1.25 and 1.35. The specific value of suitable and optimum multiple for a given test strip design can be determined using the procedures described below in the example. $t_{meas}$ can also be determined dynamically by adding a defined period of time, for example 1.5 to 2.5 seconds, to $t_{peak}$. In the general case, $t_{meas} = a_1 \times t_{peak} + a_2$ with either or both of empirically determined constants being utilized.

These two techniques can also be used in combination. In this embodiment, a test value of $t_{test}$ equal to $t_{peak}$ times a pre-determined factor or $t_{peak}$ plus a predetermined number of seconds is used as the starting point for analysis of the data points to determine the best fit to the Cottrell decay. This minimizes the data processing required, and thus accelerates the time to a result for the user.

V. Determination of $t_{meas}$ for a Plateau Analysis

Once $t_{peak}$ is determined, this value may used to dynamically determine the time $t_{meas}$ at which a plateau current should be sampled to assess glucose concentration. In a general sense, it is desirable to make the measurement at a time after $t_{peak}$ when the change in current over time is minimal. This can be accomplished in several ways, using either an analysis of collected current data in the time period following $t_{peak}$ or by setting $t_{meas}$ to be equal to $t_{peak}$ plus a predetermined number of seconds or times a predetermined factor, or a combination of both.

Establishment of $t_{meas}$ can be established by analysis of collected data points in the time period following $t_{peak}$ to determine a time when the change in the signal is substantially zero, i.e, less than 3%/sec. As a practical alternative to processing the signal in this manner, it has been found that for a specific electrochemical test strip, $t_{meas}$ can be defined as a simple multiple of $t_{peak}$ for example a multiple in the range of 1.5 to 5, for example between 3.8 and 4.7. The specific value of suitable and optimum multiple for a given test strip design can be determined using the procedures described below in the example. For plateau current measurements, $t_{meas}$ can also be determined dynamically by adding a defined period of time, for example 6 to 10 second to $t_{peak}$.

These two techniques can also be used in combination. In this embodiment, a test value of $t_{test}$ equal to $t_{peak}$ times a pre-determined factor or $t_{peak}$ plus a predetermined number of seconds is used as the starting point for analysis of the data points to determine the point when threshold slope is achieved, if it has not already done so. This minimizes the data processing required and thus accelerates the time to a result for the user, yet ensures that a plateau current has been established.

VI. Error Detection Based on $t_{peak}$

In accordance with an additional embodiment of the invention, $t_{peak}$ can be used independently or additionally as a basis for detecting measurement errors and returning an error rather than a result to the user.

For any given test strip, $t_{peak}$ should fall within a defined range of values. Various errors can occur, however, which will cause $t_{peak}$ to fall outside this range. For example, $t_{peak}$ may be too small if an inappropriate sample is used, for example a non-blood sample since the number of red blood cells influences $t_{peak}$ some reagent flakes off of working electrodes and is therefore closer to the counter electrode at the time of sample addition.

The observed value for $t_{peak}$ may also be too high, for example if a blood sample with too high a value for hct is used. For example, neonates may have hct values of up to 70%.

manufacturing errors that give rise to an electrode spacing that is too large.

The actual values that are appropriate for $t_{peak}$ are strip-dependent and are therefore appropriately determined empirically by simulating errors of the type described above.

The method of the invention may include the step of comparing the determined value of $t_{peak}$ to a predetermined range, and returning an error message when the determined value falls outside of the range. Further, this evaluation can be used separately, even in meters where the time for taking the measurement is not dynamically determined.

VI. Apparatus of the Invention

The method of the invention can be used with any strip that has a working and counter electrodes, and a diffusible mediator in one redox state (oxidized or reduced) that is initially deposited on or in the vicinity of only one electrode (the working electrode) wherein the positioning of the electrodes and the mobility of the mediator are such that mediator will dissolve and diffuse from the working electrode to the counter electrode during the time scale of the measurement, in combination with a meter apparatus that can receive the strip and provide the necessary applications of voltage and signal processing. Such a meter also forms an aspect of the present invention. Thus, the invention provides a meter for receiving an electrochemical test strip having electrodes and providing a determination of an analyte in a sample applied to the electrochemical test strip when received in the meter, said meter comprising (a) a housing having a slot for receiving an electrochemical test strip;

(b) communications means for receiving input from and communicating a result to a user; and (c) means for determining $t_{peak}$ and dynamically determining $t_{meas}$ based upon the determined value of $t_{peak}$.

Figure 5:
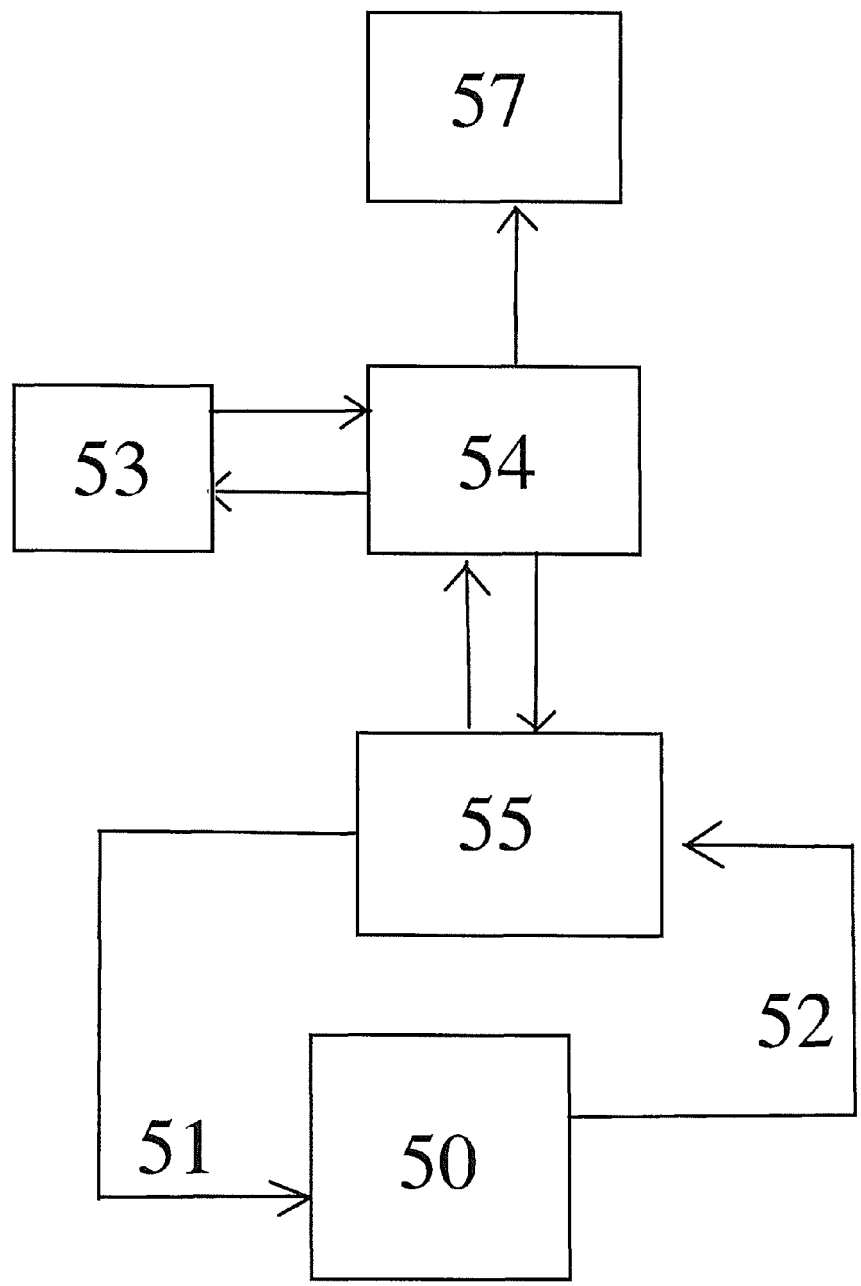
FIG. 5 shows the operation of the meter of the invention in schematic form.

FIG. 5 shows a schematic representation of the operation of a meter in accordance with the invention. As shown in FIG. 5, potential 51 is generated by circuit 55 and applied to a test strip 50. This results in a current signal 52 which is passed stored at 53. During or subsequent to this storage process, the processor 54 evaluates the characteristics of the current signal and determines $t_{peak}$ $t_{peak}$ and from makes determination of $t_{meas}$. Based on the value of $t_{meas}$ appropriate stored current data is retrieved from storage 53, processed by processor 54 to determine a result with is sent to display 57.

Figure 6:
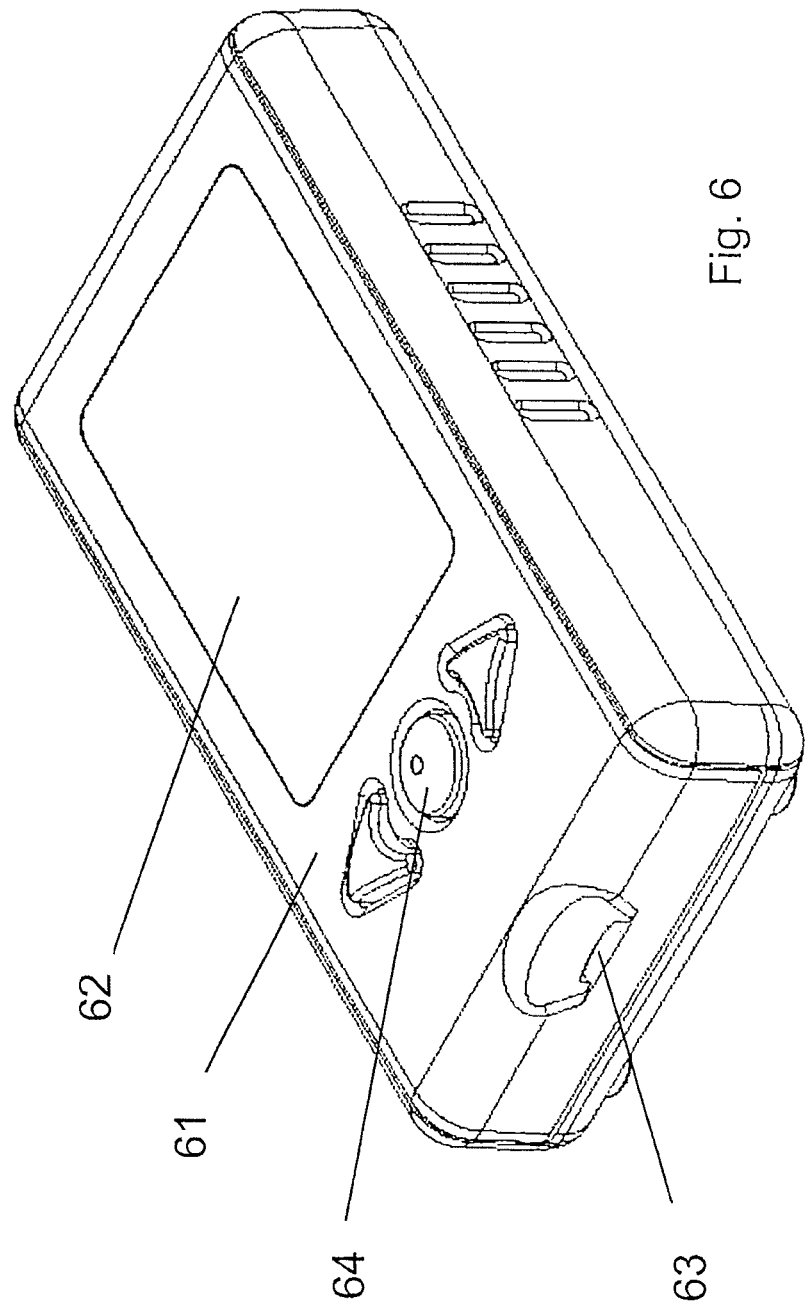
FIG. 6 shows an exterior view of a meter.

FIG. 6 shows an external view of a meter in accordance with the invention. The meter has a housing 61, and a display 62. The housing 61 has a slot 63, into which a test strip is inserted for use. The meter may also have a button 64 for signaling the start of the measurement cycle, or may have an internal mechanism for detecting the insertion of a test strip or the application of a sample. Such mechanisms are known in the art, for example from U.S. Pat. Nos. 5,266,179; 5,320,732; 5,438,271 and 6,616,819, which are incorporated herein by reference. In the meter of the invention, buttons, displays such as LCD displays, rf, infrared or other wireless transmitters, wire connectors such as USB, parallel or serial connections constitute means for receiving input from and communicating a result to a user, and can be used individually and in various combinations.

Figure 7:
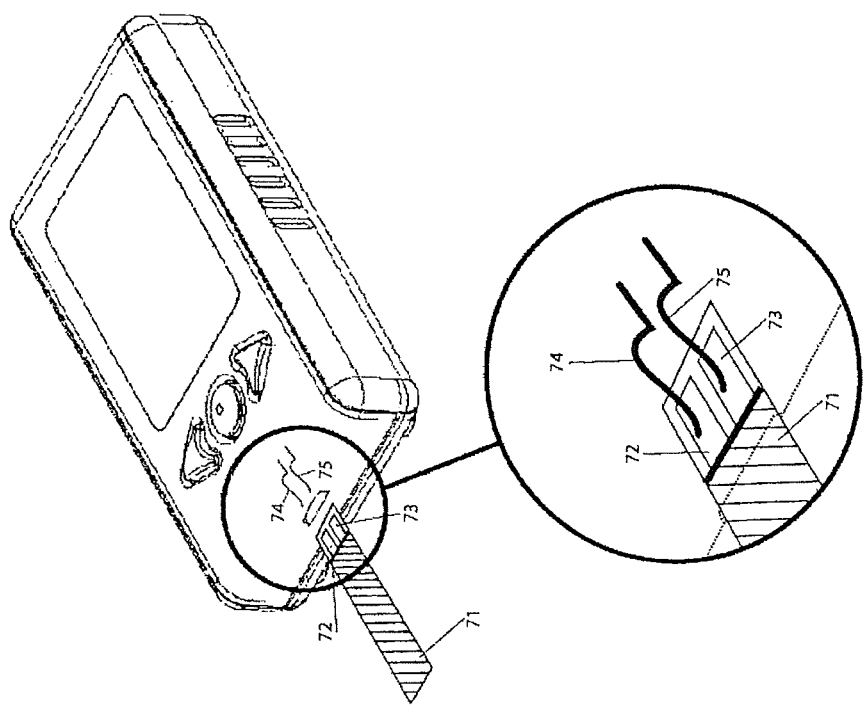
FIG. 7 shows connection of a test strip and connectors in a meter.

Internally, as schematically presented in FIG. 7, the meter of the invention comprises a potentiostat 71 capable of operating in amperometric mode, a data-storage device 72, such as a flash memory, EEPROMs or battery-backed RAM, and a microprocessor 73 for controlling the potentiostat 71, processing data, and transmitting a communication/display to the user interface 74. The microprocessor 73 in the apparatus of the invention is programmed to determine $t_{peak}$ and then establish $t_{meas}$ based on the determined $t_{peak}$.

The meter may further comprise means for comparing the determined value of $t_{peak}$ to a predetermined range, and returning an error message when the determined value falls outside of the range. Exemplary means for this purpose are a programmed microprocessor that retrieves the range from memory and performs the comparison.

In one embodiment of the invention, the microprocessor 73 sets the value of $t_{meas}$ to $t_{peak}$ times a pre-determined factor determined by testing of electrochemical test strips of the same type as being used in the meter.

In one embodiment of the invention, the microprocessor 73 samples the current over a range of time determined as a low and a high multiple of $t_{peak}$, these data points to determine the data point where the second derivative of the current versus time plot is closest to zero, and uses this data point to determine the glucose concentration.

Example 1

A meter with dynamic determination of $t_{meas}$ using tpeak was used to evaluate finger-stick blood samples from a number diabetic patients, with no selection based on ages, genders, or ethnicity. The samples thus encompassed a good spread of blood physiologies, including different hct levels and different glucose levels. The test strip employed had facing screen printed carbon electrodes, and a nominal sample volume of 625 nanoliters. Since $t_{peak}$ depends on both mobility of mediator (affected by hct) and by the concentration of glucose (if there is higher glucose, then more of the mediator must diffuse to the counter electrode, thereby taking more time), this sampling produced signals with a good range of different $t_{peak}$ values.

The meter did the measurement, which was to do amperometry until enough Cottrell data was gathered ($t_{meas}$ region), and made glucose determinations based on the Cottrell data. The meter also stored the total time from sample introduction to LCD display of reading. This information is summarized in FIG. 4 which is a histogram showing how many measurements (out of 110) were within each time range. Most readings were between 6 to 7 seconds, with an overall average of ~6.4 sec.

Example 2

In order to determine the appropriate coefficient to apply in modifying $t_{peak}$ to determine $t_{meas}$, measurements are taken on matrix of samples with a range of hct and glucose concentrations in amperometric mode. An exemplary matrix is —hct=0, 20, 40, 60, 65%
—[glu]=~2 mM up to ~30 mM although the important thing is to select ranges that are representative of typical users. For each each glu/hct combination, replicate measurements are made, and the amperometric data (current vs. time) is compiled.

The data is processed in any of several different ways (as described in FIGS. 3A-D to arrive a value of $t_{meas}$. for each data point. The relationship between $t_{peak}$ and $t_{meas}$ for all the data spanning the range of glucose concentration and hct levels is plotted. The plotted data points are then fit to a linear model, indicating whether the correction is best modeled as an additive correction, a multiplier, or both. Other models with additional terms may also be employed in fitting the data.

What is claimed is:

1. A method for detecting an error condition in an electrochemical determination of an analyte in a sample applied to an electrochemical test strip disposed in an analyte detection apparatus, comprising the steps of:
   (a) introducing a sample to be evaluated into an electrochemical test strip having working and counter electrodes;
   (b) applying a potential between the electrodes sufficient to generate a diffusion-limited current when analyte is present in the sample;
   (c) dynamically determining a time, $t_{peak}$, as the time when diffusion limiting current at the counter electrode is established;
   (d) comparing the determined value of $t_{peak}$ to a predetermined range, and returning an error message when the determined value falls outside of the range.

2. The method of claim 1, wherein the sample is a blood sample.

3. The method of claim 2, wherein the electrochemical test strip is a test strip for determination of glucose in the sample.

4. The method of claim 1, wherein the electrochemical test strip is a test strip for determination of glucose in the sample.

5. A meter for receiving an electrochemical test strip having electrodes and providing a determination of an analyte in a sample applied to the electrochemical test strip when received in the meter, said meter comprising
   (a) a housing having a slot for receiving an electrochemical test strip;
   (b) communications means for receiving input from and communicating a result to a user;
   (c) means for determining a time, wherein the means determines the time when diffusion limiting current at the counter electrode is established, referred to as $t_{peak}$; and
   (d) means for comparing the determined value of $t_{peak}$ to a predetermined range and returning an error message when the determined value falls outside of the range.

* * * * *